United States Patent
Shuros et al.

(10) Patent No.: US 8,600,499 B2
(45) Date of Patent: Dec. 3, 2013

(54) METHOD AND DEVICE FOR CARDIAC VASOACTIVE THERAPY

(75) Inventors: Allan C. Shuros, St. Paul, MN (US); Shantha Arcot-Krishnamurthy, Roseville, MN (US); Joseph Walker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 952 days.

(21) Appl. No.: 11/566,896

(22) Filed: Dec. 5, 2006

(65) Prior Publication Data
US 2008/0132972 A1    Jun. 5, 2008

(51) Int. Cl.
*A61N 1/362* (2006.01)

(52) U.S. Cl.
USPC .................. 607/11; 607/9; 607/10

(58) Field of Classification Search
USPC ................. 607/2, 42, 60, 62, 9–11
See application file for complete search history.

(56) References Cited

U.S. PATENT DOCUMENTS

| | | | |
|---|---|---|---|
| 5,135,004 | A | 8/1992 | Adams et al. |
| 5,181,519 | A | 1/1993 | Bible |
| 5,199,428 | A | 4/1993 | Obel et al. |
| 5,226,424 | A | 7/1993 | Bible |
| 5,531,768 | A | 7/1996 | Alferness |
| 6,021,350 | A | 2/2000 | Mathson |
| 6,108,577 | A | 8/2000 | Benser |
| 6,112,116 | A | 8/2000 | Fischell et al. |
| 6,128,526 | A | 10/2000 | Stadler et al. |
| 6,256,538 | B1 | 7/2001 | Ekwall |
| 6,272,379 | B1 | 8/2001 | Fischell et al. |
| 6,339,720 | B1 | 1/2002 | Anzellini et al. |
| 6,368,284 | B1 | 4/2002 | Bardy |
| 6,397,109 | B1 | 5/2002 | Cammilli et al. |
| 6,468,263 | B1 | 10/2002 | Fischell et al. |
| 6,507,753 | B1 | 1/2003 | Xue et al. |
| 6,532,381 | B2 | 3/2003 | Bayer et al. |
| 6,609,023 | B1 | 8/2003 | Fischell et al. |
| 6,628,988 | B2 | 9/2003 | Kramer et al. |
| 6,827,690 | B2 | 12/2004 | Bardy |
| 6,865,420 | B1 | 3/2005 | Kroll |
| 6,882,883 | B2 | 4/2005 | Condie et al. |

(Continued)

FOREIGN PATENT DOCUMENTS

| | | |
|---|---|---|
| JP | 2008-523533 A | 7/2008 |
| WO | WO-2006/124729 A2 | 11/2006 |
| WO | WO-2007/013065 A2 | 2/2007 |

OTHER PUBLICATIONS

Koizumi, T., "Improvement of Left Ventricular Dysfunction During Exercise by Walking in Patients With Successful Percutaneous Coronary Intervention for Acute Myocardial Infarction.", *Circ J.*, 67(3), (Mar. 2003), 233-237.

(Continued)

*Primary Examiner* — Christopher D Koharski
*Assistant Examiner* — Michael D Abreu
(74) *Attorney, Agent, or Firm* — Schwegman Lundberg & Woessner, P.A.

(57) ABSTRACT

A method and device for treating myocardial ischemia in which an implantable pulse generator delivers electrical stimulation to electrodes disposed near a coronary artery. The stimulation parameters may be adjusted to produce vasodilation and/or vasoconstriction of the artery. The device may be configured to operate in a vasodilation and/or vasoconstriction mode in accordance with specified entry and exit conditions.

22 Claims, 7 Drawing Sheets

(56) References Cited

U.S. PATENT DOCUMENTS

| | | |
|---|---|---|
| 6,913,577 B2 | 7/2005 | Bardy |
| 6,915,160 B2 | 7/2005 | Auricchio et al. |
| 6,965,797 B2 | 11/2005 | Pastore et al. |
| 6,973,349 B2 | 12/2005 | Salo |
| 6,985,771 B2 | 1/2006 | Fischell et al. |
| 7,010,345 B2 | 3/2006 | Hill et al. |
| 7,066,891 B2 | 6/2006 | Stadler et al. |
| 7,072,711 B2 | 7/2006 | Girouard et al. |
| 7,254,440 B1 | 8/2007 | Kroll |
| 7,272,436 B2 | 9/2007 | Gill et al. |
| 7,297,114 B2 | 11/2007 | Gill et al. |
| 7,299,087 B2 | 11/2007 | Bardy |
| 7,340,303 B2 | 3/2008 | Zhu |
| 7,369,892 B2 | 5/2008 | Ferek-Petric |
| 7,437,191 B2 | 10/2008 | Pastore et al. |
| 7,460,906 B2 | 12/2008 | Libbus |
| 7,486,991 B2 | 2/2009 | Libbus et al. |
| 7,512,438 B2 | 3/2009 | Fischell et al. |
| 7,524,287 B2 | 4/2009 | Bharmi |
| 7,558,623 B2 | 7/2009 | Fischell et al. |
| 7,577,478 B1 | 8/2009 | Kroll et al. |
| 2003/0023175 A1 | 1/2003 | Arzbaecher et al. |
| 2003/0083698 A1 | 5/2003 | Whitehurst et al. |
| 2003/0149354 A1 | 8/2003 | Bakharev |
| 2003/0149423 A1 | 8/2003 | Fischell et al. |
| 2003/0191402 A1 | 10/2003 | Arzbaecher et al. |
| 2004/0059238 A1 | 3/2004 | Fischell et al. |
| 2005/0043639 A1 | 2/2005 | Fischell |
| 2005/0043675 A1 | 2/2005 | Pastore et al. |
| 2005/0065445 A1 | 3/2005 | Arzbaecher et al. |
| 2005/0075673 A1 | 4/2005 | Warkentin et al. |
| 2005/0085736 A1 | 4/2005 | Ambrose et al. |
| 2005/0137483 A1 | 6/2005 | Fischell et al. |
| 2005/0143779 A1 | 6/2005 | Libbus |
| 2005/0143785 A1 | 6/2005 | Libbus |
| 2005/0149129 A1 | 7/2005 | Libbus et al. |
| 2005/0149130 A1 * | 7/2005 | Libbus .............................. 607/9 |
| 2005/0256417 A1 | 11/2005 | Fischell et al. |
| 2005/0288721 A1 | 12/2005 | Girouard et al. |
| 2006/0206158 A1 | 9/2006 | Wu et al. |
| 2006/0247686 A1 | 11/2006 | Girouard et al. |
| 2006/0253044 A1 | 11/2006 | Zhang et al. |
| 2006/0259088 A1 | 11/2006 | Pastore et al. |
| 2006/0265020 A1 | 11/2006 | Fischell et al. |
| 2007/0093720 A1 | 4/2007 | Fischell et al. |
| 2007/0208263 A1 | 9/2007 | John et al. |
| 2007/0249944 A1 | 10/2007 | Fischell et al. |
| 2007/0249947 A1 | 10/2007 | Fischell et al. |
| 2007/0276453 A1 | 11/2007 | Hill et al. |
| 2007/0282380 A1 | 12/2007 | Brooke et al. |
| 2007/0293775 A1 | 12/2007 | Fischell et al. |
| 2007/0293778 A1 | 12/2007 | Fischell et al. |
| 2008/0058660 A1 | 3/2008 | Fischell et al. |
| 2008/0058661 A1 | 3/2008 | Bardy |
| 2008/0058881 A1 | 3/2008 | Wagner et al. |
| 2008/0064973 A1 | 3/2008 | Fischell et al. |
| 2008/0091138 A1 | 4/2008 | Pastore et al. |
| 2008/0139954 A1 | 6/2008 | Day et al. |
| 2008/0183091 A1 | 7/2008 | Fischell et al. |
| 2008/0188762 A1 | 8/2008 | John et al. |
| 2008/0188763 A1 | 8/2008 | John et al. |
| 2009/0048528 A1 | 2/2009 | Hopenfeld et al. |
| 2009/0048641 A1 | 2/2009 | Libbus |
| 2009/0076403 A1 | 3/2009 | Hopenfeld |
| 2009/0082682 A1 | 3/2009 | Fischell et al. |
| 2009/0143835 A1 | 6/2009 | Pastore et al. |
| 2009/0171228 A1 | 7/2009 | Fischell et al. |
| 2009/0192397 A1 | 7/2009 | Fischell et al. |
| 2009/0216141 A1 | 8/2009 | Fischell et al. |

OTHER PUBLICATIONS

Wolfel, E. E., "Marathoners or Couch Potatoes: What is the Role of Exercise in the management of Heart Failure?", *Current Heart Failure Reports*, 2(1), (Mar. 2005), 25-34.

International Application No. PCT/US2007/024730, International Search Report mailed Jun. 5, 2008, 4 pgs.

International Application No. PCT/US2007/024730, Written Opinion mailed Jun. 5, 2008, 5 pgs.

"European Application Serial No. 07867604.6, Response filed Nov. 30, 2010 to Office Action mailed Sep. 23, 2010", 9 pgs.

"European Application Serial No. 07867604.6, Communication dated Jul. 22, 2009", 2 pgs.

"European Application Serial No. 07867604.6, Office Action mailed Sep. 23, 2010", 4 pgs.

"European Application Serial No. 07867604.6, Response filed Aug. 19, 2009 to Communication dated Jul. 22, 2009", 9 pgs.

"Japanese Application Serial No. 2009-540244, Office Action mailed Jul. 23, 2012", (w/ English Translation), 4 pgs.

\* cited by examiner

METHOD AND DEVICE FOR CARDIAC VASOACTIVE THERAPY

RELATED CASES

This application is related to U.S. Pat. Nos. 6,628,988, 6,973,349, 6,915,160, and 6,965,797 and to U.S. patent application Ser. No. 11/427,517 filed on Jun. 29, 2006 and Ser. No. 11/541,837, filed on Oct. 2, 2006, all of which are hereby incorporated by reference in their entirety.

FIELD OF THE INVENTION

This invention pertains to cardiac rhythm management devices such as pacemakers and other implantable devices.

BACKGROUND

Myocardial ischemia refers to a condition in which the blood supply to a region of myocardium (i.e., heart muscle) becomes so compromised that the region is not supplied with adequate oxygen for oxidative metabolism. Ischemia, as opposed to hypoxia without any reduction in perfusion, is also accompanied by reduced removal of metabolic by-products. The heart is an aerobic organ that generates energy almost exclusively from the oxidation of substrates with oxygen delivered by the blood. It can develop only a small oxygen debt and is therefore extremely sensitive to disruptions in blood supply. Myocardial ischemia occurs when there is an imbalance between oxygen supply and demand as a result of increased myocardial oxygen demand, reduced myocardial oxygen supply, or both. Myocardial ischemia causes many patients to experience chest pain or discomfort, referred to as angina pectoris. Angina pectoris can serve as a useful warning of insufficient myocardial perfusion that can lead to the more serious situation such as a heart attack or cardiac arrhythmia.

Coronary artery disease (CAD) occurs when the coronary arteries that supply blood to the myocardium become hardened and narrowed due to the buildup of atherosclerotic plaque. An atherosclerotic plaque is the site of an inflammatory reaction within the wall of an artery and is made up of a core containing lipid and inflammatory cells surrounded by a connective tissue capsule. A myocardial infarction (MI), or heart attack, occurs when atherosclerotic plaque within a coronary artery ruptures and leads to the clotting of blood (thrombosis) within the artery by exposing the highly thrombogenic lipid core of the plaque to the blood. The complete or nearly complete obstruction to coronary blood flow can damage a substantial area of heart tissue and cause sudden death, usually due to an abnormal heart rhythm that prevents effective pumping.

In the presence of coronary obstruction due to CAD, an increase in myocardial oxygen requirements brought about by, for example, physical exertion or emotional distress, can cause a temporary imbalance in oxygen supply and demand. Such demand ischemia can cause what is called exertional anginal or chronic stable angina. In other situations, an imbalance can occur acutely due to a sudden reduction in blood flow, sometimes referred to as supply ischemia. An acute blood flow disruption may be secondary to a coronary vasospasm, causing what is called unstable angina. As noted above, an acute blood flow disruption can also result from coronary thrombosis, causing an MI. Myocardial ischemia often results from both an increase in oxygen demand and a reduction in supply.

DETAILED DESCRIPTION

Figure 1:
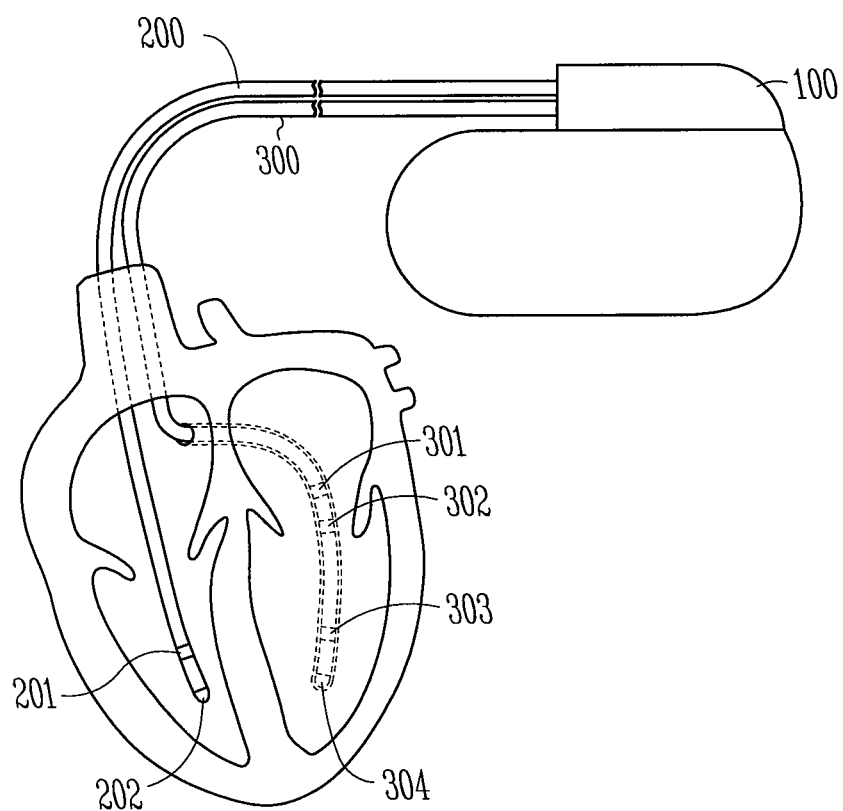
FIG. 1 illustrates the physical configuration of an exemplary pacing device.

Myocardial ischemia is usually treated with pharmacological agents that act to either increase myocardial perfusion or reduce myocardial oxygen demand. Surgical revascularization procedures may also be performed to increase blood supply. Described herein is an alternative intervention for treating myocardial ischemia that employs electrical stimulation such as may be delivered by an implantable cardiac device to produce vasodilation and/or vasoconstriction of one or more coronary arteries.

Vasoactive Electrical Stimulation of Coronary Arteries

As the term is used herein, vasoactive therapy is electrical stimulation applied to a blood vessel in a manner that produces either vasoconstriction or vasodilation. It has been found experimentally that electrical stimulation pulses applied to an artery may produce constriction of the artery when the pulses are applied at one frequency and dilation of the artery when the pulses are applied at another frequency. For example, experiments involving aortic stimulation have found that low frequency stimulation (e.g., at approximately 1 Hz) leads to dilation while high frequency stimulation (e.g., at approximately 16 Hz) leads to constriction. The stimulation parameters that produce vasodilation or vasoconstriction may vary with the particular artery and with the particular patient. Described herein is an implantable pulse generator device and lead(s) system that may be configured for stimulation of one or more coronary arteries in order to produce vasodilation and/or vasoconstriction. The device may deliver vasodilation stimulation in order to relieve anginal symptoms and/or prevent myocardial infarction and may be delivered, for example, in response to one or more sensed variables that indicate myocardial ischemia and/or in response to a command received via telemetry or by other means. The device may deliver vasoconstriction stimulation on an intermittent basis according to a defined schedule and/or in response to one or more sensed variables in order to intentionally stress and precondition the heart. This vasoconstriction produces intermittent ischemia in order to produce a therapeutic effect similar to exercise. Such intermittent episodes of myocardial ischemia may enable the heart to better withstand subsequent episodes of naturally occurring ischemia and/or induce angiogenesis to improve the heart's blood supply.

In order for an implantable pulse generator to deliver vasoactive therapy to the heart, a stimulation electrode may be positioned epicardially directly on a coronary artery. An alternative approach involves placing a stimulation lead in the coronary sinus or a cardiac vein in proximity to a targeted artery such as the left circumflex coronary artery or the left anterior descending coronary artery. The stimulation electrode could also be placed in the right ventricle to target the right coronary artery using similar methods. Stimulation parameters may then be adjusted while monitoring myocardial blood flow (e.g., by means of coronary angiography or an electrocardiogram) to ascertain the optimal parameters for producing vasoconstriction and/or vasodilation in a particular patient. Such stimulation parameters could include pulse frequency, stimulation polarity (anodal or cathodal), pulse amplitude, pulse width, stimulation vector, and stimulation burst duration. Simulation could be timed with the cardiac cycle to occur selectively during systolic or diastolic periods. The information about the systolic and diastolic periods could be obtained from local electrogram signals, impedance measurements, heart sounds, pressure signals, or ECG's.

As described above, an implantable cardiac device may be configured with one or more electrodes disposed at a site(s) in proximity to a coronary artery. The device may then be programmed to operate in a vasodilation mode that delivers stimulation pulses in a manner that produces dilation of the coronary artery. In one embodiment, the stimulation pulses may be delivered while the heart is refractory as determined by sensed cardiac electrical activity. In another embodiment, either in addition to or instead of delivering stimulation while the heart is refractory, the stimulation pulses may timed with the cardiac cycle to occur selectively during systolic or diastolic periods as determined from local electrogram signals, impedance measurements, heart sounds, or pressure signals. The vasodilation increases myocardial blood flow and reduces any ischemia that may be present. The device may be programmed to operate in the vasodilation mode intermittently where the device reverts to a normal mode when the vasodilation mode terminates. In the normal and/or vasodilation modes the device may concomitantly deliver additional therapies such as bradycardia or cardiac resynchronization pacing and/or anti-tachyarrhythmia therapies such as anti-tachycardia pacing and cardioversion/defibrillation. The device may switch from the normal mode to the vasodilation mode in accordance with one or more entry conditions such as: 1) actuation of a patient-operated switch that the patient may operate when angina occurs, 2) receipt of a telemetry command to initiate the mode, and/or 3) detection of the presence of myocardial ischemia by the device in accordance with a sensed variable that is correlated with the presence of myocardial ischemia. Examples of sensed variables reflective of myocardial ischemia include features derived from sensed cardiac electrical activity, non-electrical measures (e.g., heart sounds or pressure signals), and/or, in a patient with demand ischemia, variables related to exertion level such as heart rate, minute ventilation, and activity level. The vasodilation mode may also be caused to terminate upon detection of one or more specified events or conditions, referred to as exit conditions. Such exit conditions could include, for example, non-detection of the presence of myocardial ischemia, a lapsed time interval, actuation of a patient-operated switch, and/or receipt of a telemetry command to terminate the mode.

As mentioned above, another use of vasoactive therapy in the treatment of myocardial ischemia is to intentionally stress the heart by intermittently causing a low level of myocardial ischemia, thereby promoting angiogenesis and possibly preconditioning the heart to better withstand the effects of a subsequent ischemic episode. Accordingly, the device may be configured to intermittently switch from a normal mode or vasodilation mode to a vasoconstriction mode that delivers stimulation to one or more coronary artery sites in a manner that causes vasoconstriction. As with the vasodilation stimulation discussed above, vasoconstriction stimulation may be delivered during a cardiac refractory period and/or timed with the cardiac cycle to occur selectively during systolic or diastolic periods. Intermittent switching to the vasoconstriction mode may be controlled in accordance with one or more entry conditions and one or more exit conditions, where such entry and exit conditions may include lapsed time intervals, heart rate, activity level as measured by an accelerometer, and minute ventilation. Since the vasoconstriction mode is designed to produce low level myocardial ischemia, it is desirable for it to only be employed when the patient is at rest and not experiencing an ischemic episode by reason of either increased metabolic demand or decreased blood supply. For example, an entry condition for entering the vasoconstriction mode could be the measured heart rate and/or exertion level being below some specified threshold value, and an exit condition for terminating the vasoconstriction mode could be the measured heart rate and/or exertion level being above some specified threshold value. Additional entry and exit conditions could be lapsed time intervals based upon a defined schedule so that the vasoconstriction mode is only entered at certain times of the day and/or is limited in duration.

Exemplary Implantable Device

FIG. 1 shows an implantable pulse generator 100 for delivering vasoactive therapy to the heart as well as possibly other types of therapy. Implantable cardiac devices such as pacemakers are typically placed subcutaneously or submuscularly in a patient's chest with leads threaded intravenously into the heart to connect the device to electrodes disposed within a heart chamber that are used for sensing and/or stimulation. Electrodes may also be positioned on the epicardium by various means. FIG. 1 shows the exemplary device having two leads 200 and 300, each of which is a multi-polar (i.e., multi-electrode) lead having electrodes 201-202 and 301-304, respectively. The electrodes 201-202 are disposed in the right ventricle in order to sense cardiac electrical activity as well as possibly provide pacing therapy. The electrodes 301-304 are disposed in the coronary sinus in order to stimulate the left circumflex coronary artery. The device could be configured with additional leads and/or electrodes and/or pacing vectors in order to stimulate additional arterial sites and/or to provide pacing therapy to one or more myocardial sites. The device senses intrinsic cardiac electrical activity through one or more sensing channels and delivers vasoactive stimulation (or pacing pulses) through one or more stimulation channels, where each such channel incorporates one or more of the electrodes, pacing configurations (i.e., unipolar or bipolar) and pacing vectors. A programmable electronic controller controls the delivery of vasoactive stimulation pulses and/or pacing pulses in response to lapsed time intervals and/or sensed cardiac electrical activity (i.e., intrinsic heart beats not as a result of a pacing pulse). As mentioned above, it may be desirable for vasoactive stimulation pulses to be delivered while the heart is refractory. The refractory period of the heart may be determined as a specified time period subsequent to a ventricular sense or a ventricular pace. Depending on the cardiac vessel of interest, the stimulation could be based on flow patterns in the vessel rather than refractory periods. Such flow patterns could be inferred from cardiac electrical activity or could be measured via an impedance sensor for measuring blood flow. Vasoactive stimulation could also be delivered in timed relation to specific portions of the mechanical cardiac cycle as determined from an impedance measurement indicative of cardiac blood flow. Coronary blood flow is greatest during diastole, for example, and it may be desirable to dilate or constrict a coronary vessel during this time.

Figure 2:
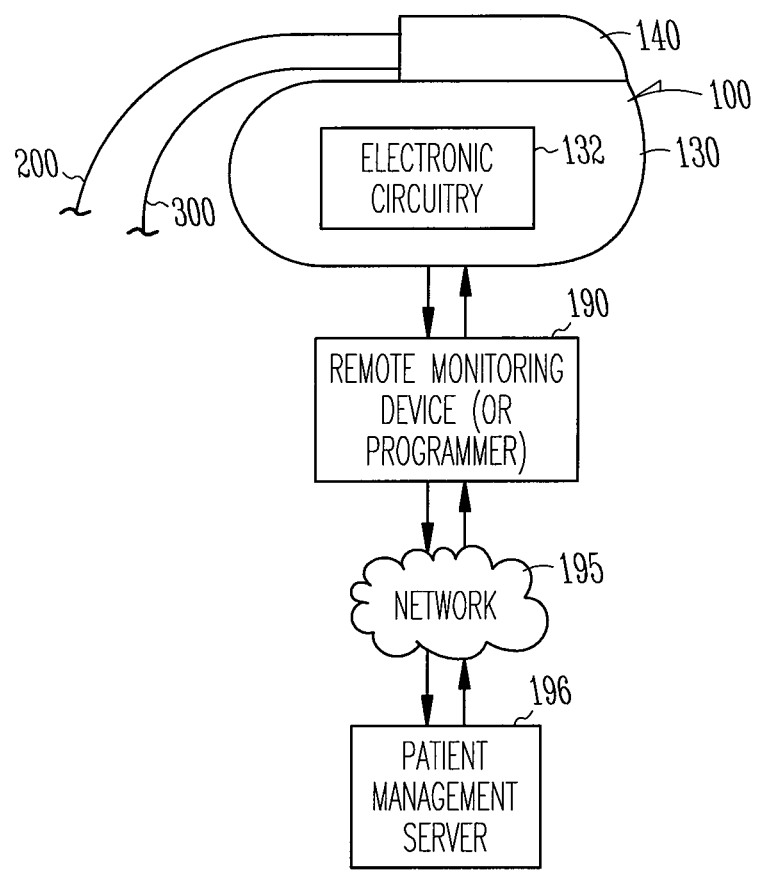
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
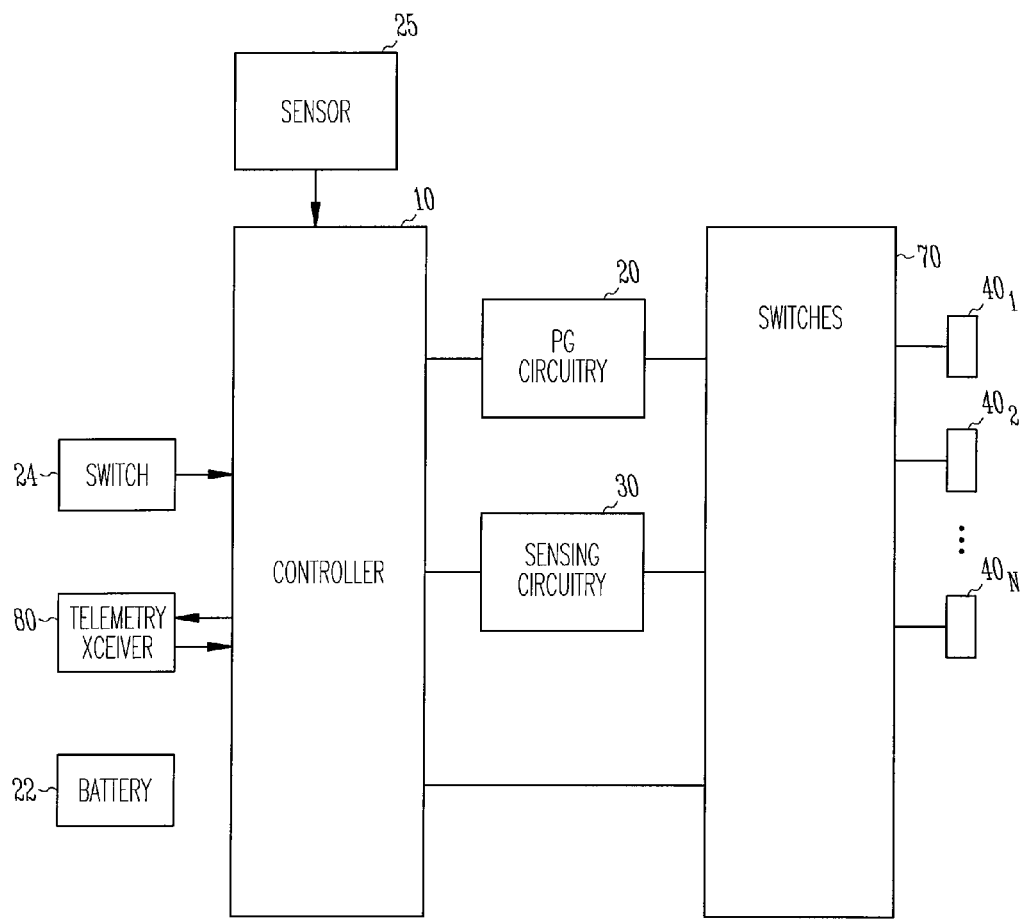
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 30 and pulse generation circuitry 20 by which the controller interprets sensing signals and controls the delivery of stimulation pulses. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers stimulation pulses to electrodes disposed for vasoactive stimulation or pacing and includes capacitive discharge pulse generators, registers for controlling the pulse generators, and registers for adjusting stimulation parameters such as pulse energy (e.g., pulse amplitude and width) and frequency. Stimulation parameters may be adjusted by programming the device via the telemetry interface in accordance with electrophysiological and/or angiographic testing to determine appropriate parameters for producing vasoconstriction and/or vasodilation of the targeted artery. The pulse generation circuitry may also include a shocking pulse generator for delivering a defibrillation/cardioversion shock via a shock electrode upon detection of a tachyarrhythmia. A telemetry transceiver 80 is interfaced to the controller which enables the controller to communicate with an external programmer and/or a remote monitoring unit. A magnetically or tactilely actuated switch 24 is also shown as interfaced to the controller to allow the patient to signal certain conditions or events to the implantable device. Also interfaced to the controller are one or more sensors 25 for sensing physiological variables that may be used to control pacing or vasoactive stimulation such as activity level (e.g., an accelerometer), heart rate, minute ventilation, thoracic impedance indicating cardiac blood flow and/or timing of cardiac cycles, cardiac output, blood pressure, blood oxygen, blood pH, blood enzymes (e.g. CK-MB, troponin, etc) and myocardial contractility (e.g., as indicated by the maximum dP/dt measured by an arterial pressure sensor).

A stimulation channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or stimulation channel, respectively. The device may be equipped with any number of pulse generators, amplifiers, and electrodes that may be combined arbitrarily to form sensing or stimulation channels and vectors. A stimulation channel may be configured as a vasoactive stimulation channel or a pacing channel. The device illustrated in FIG. 3 may be configured with multiple sensing and/or stimulation channels that may be either atrial or ventricular sensing/pacing channels or vasoactive stimulation channels depending upon the location of the electrode. It is also possible for a stimulation channel to act as either a vasoactive stimulation channel or a pacing channel depending upon the timing and type of stimulation pulses delivered. Configuration of stimulation and sensing channels may be performed via an external programmer communicating through the telemetry interface as well as automatically by the device when switching to or from different operating modes.

The switch matrix 70 also allows selected ones of the available implanted electrodes to be incorporated into sensing and/or stimulation channels in either unipolar or bipolar configurations. A bipolar sensing or stimulation configuration refers to the sensing of a potential or output of a stimulation pulse between two closely spaced electrodes, where the two electrodes are usually on the same lead (e.g., a ring and tip electrode of a bipolar lead or two selected electrodes of a multi-polar lead). A unipolar sensing or stimulation configuration is where the potential sensed or the stimulation pulse output by an electrode is referenced to the conductive device housing or another distant electrode.

Detection of Myocardial Ischemia

When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. Ischemia and infarction can also affect the magnitude of depolarization and the velocity at which it travels through the myocardium. All of these effects result in abnormal changes in the electrical potentials produced by cardiac excitation as reflected by either a surface electrocardiogram or an intracardiac electrogram. The device may therefore be configured to detect the presence of myocardial ischemia from one or more sensed variables related to cardiac electrical activity.

The device may be configured to detect cardiac ischemia from a morphology analysis of an electrogram collected during an intrinsic or a paced beat, the latter sometimes referred to as an evoked response. As aforesaid, a current of injury results in an abnormal change in the electrical potentials measured by an intracardiac electrogram. If the abnormal depolarization in the ventricles lasts for the entire cardiac cycle, a zero potential is measured only when the rest of the ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic or infarcted region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered. In order for the device to detect a change in an electrogram indicative of ischemia, a recorded electrogram is analyzed and compared with a reference electrogram, which may either be a complete recorded electrogram or particular reference values representative of an electrogram. Because certain patients may always exhibit a current of injury in an electrogram (e.g., due to CAD or as a result of electrode implantation), the controller may be programmed to detect ischemia by looking for an increased current of injury in the recorded electrogram as compared with the reference electrogram, where the latter may or may not exhibit a current of injury. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present.

As mentioned previously, other sensed variables may also be indicative of the presence of myocardial ischemia, especially in patients with exertional angina. The device may therefore be programmed to detect the presence of myocardial ischemia with some degree of probability from sensed variables such as heart rate, activity level, local cardiac motion, local tissue impedance, and minute ventilation, either in addition to or instead of the techniques discussed above based upon cardiac electrical activity. To add specificity to the detection scheme, for example, the device may be programmed to detect myocardial ischemia only when a current of injury is detected and the patient's heart rate and/or exertion level (as measured by activity level or minute ventilation) is above a specified threshold value.

Exemplary Implementations

Figure 4:
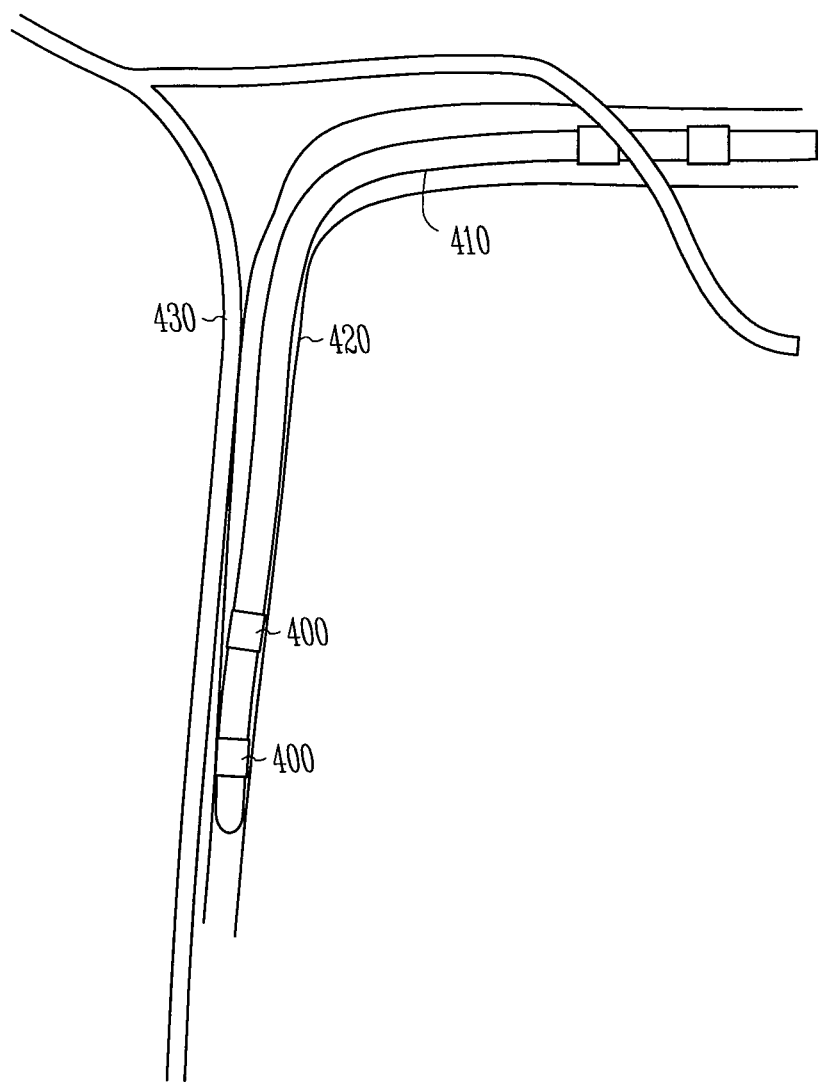
FIG. 4 shows an exemplary placement of vasoactive stimulation electrodes.
Figure 5A:
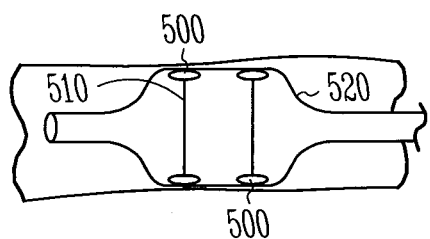
FIGS. 5A and 5B show example embodiments of vasoactive stimulation leads.
Figure 5B:
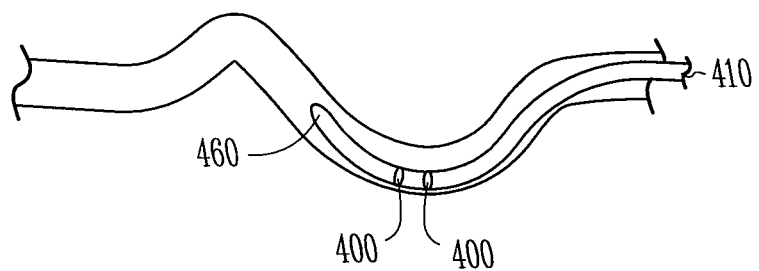

In order to implement vasoactive therapy, a cardiac device is implanted in a patient with stimulation electrodes disposed near one or more coronary arteries. FIG. 4 shows an example of bipolar stimulation electrodes 400 incorporated into a lead 410 that is inserted into the coronary sinus or a cardiac vein 420 so as to be in proximity to a branch of a coronary artery 430. The lead 410 may incorporate mechanical means to facilitate positioning the stimulation electrodes within a vein adjacent the coronary artery to be stimulated. FIG. 5A shows one embodiment in which the lead incorporates a stent 520 with electrodes 500 on struts 510 that expand against vein wall and thus press the electrodes against the adjacent artery wall. FIG. 5B shows another embodiment in which the lead 410 has a steerable tip 460 that may be maneuvered in such a way as to press the electrodes 400 against the adjacent artery wall. A stimulation lead may also be placed in the myocardium in a region determined to have microvascular dysfunction. Some patients with anginal symptoms may not have occlusive lesions in their major arteries. However, the problem arises in these patients in their microvascular circulation. The vasomodulation therapy may be applied to these patients by targeting their myocardial capillary bed.

After implantation and appropriate placement of the vasoactive stimulation electrodes, the device may then be programmed with appropriate stimulation parameters to deliver vasoconstriction and/or vasodilation stimulation. Such stimulation parameters could include pulse frequency, stimulation polarity (anodal or cathodal), pulse amplitude, pulse width, stimulation vector, and stimulation burst duration. In order to select the appropriate parameters, different stimulation parameters may be tried while monitoring the patient's coronary blood flow by, for example, coronary angiography, ultrasonic flow sensing, perfusion scanning, magnetic resonance angiography, or electrocardiography. The stimulation parameters appropriate for the vasodilation and/or vasoconstriction modes may then be programmed into the device. The device may be further programmed to automatically adjust the stimulation parameters for the vasodilation and/or vasoconstriction modes in accordance with one or more variables sensed by the device that are related to myocardial ischemia in order to increase or decrease the amount of vasoactive therapy delivered as appropriate. A look-up table may be constructed for this purpose that maps different values of the sensed variable to different values of the stimulation parameters by monitoring the sensed variable and coronary blood flow as the stimulation parameters are varied. The device may then be configured to automatically adjust the stimulation parameters in either the vasodilation or vasoconstriction modes in closed-loop fashion in accordance with the sensed variable(s).

An exemplary implantable cardiac device for delivering vasoactive therapy is equipped with one or more leads having stimulation electrodes that can be placed either endocardially or epicardially in proximity to a coronary artery. The stimulation electrodes so disposed are then configured into one or more vasoactive stimulation channels. In order to localize the stimulation, the stimulation channels are preferably configured to deliver bipolar stimulation to the targeted arterial site(s). In an exemplary electrode placement for a vasoactive stimulation channel, a pair of bipolar stimulation electrodes is disposed in the coronary sinus or a cardiac vein that communicates with the coronary sinus so as to stimulate a branch of the left coronary artery. The device may then deliver stimulation pulses through the vasoactive stimulation channel(s), where the stimulation parameters are selected to produce either vasodilation or vasoconstriction. In order to prevent myocardial capture, the vasoactive stimulation pulses may be delivered synchronously with detected cardiac electrical activity during a time when the heart is refractory. For this purpose, the same electrode(s) used for vasoactive stimulation or different electrodes may be incorporated into a unipolar or bipolar ventricular sensing channel. Vasoactive stimulation pulses may then be delivered as a burst of pulses during a specified time period following detection of a ventricular sense (i.e., an R wave). In the case where the device also delivers ventricular pacing therapy, the burst of vasoactive stimulation pulses may be similarly delivered during a specified time period after a ventricular pacing pulse.

Figure 6:
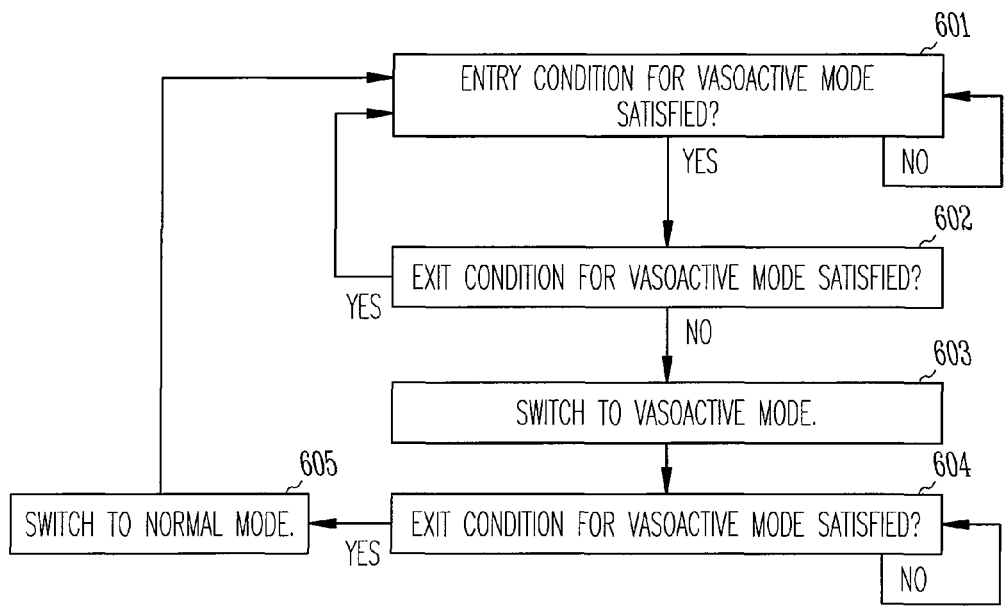
FIG. 6 illustrates an exemplary algorithm employing entry and exit conditions for switching to a vasoactive mode.

The device could be configured to deliver vasodilation or vasoconstriction stimulation pulses continuously but, in most cases, it is preferable to configure the device to deliver such stimulation on an intermittent basis. Accordingly, the device may be configured to operate in either a normal mode where no vasoactive therapy is delivered or a vasodilation and/or vasoconstriction mode where vasoactive stimulation pulses are delivered. The device may also deliver other kinds of therapy such as bradycardia pacing or cardiac resynchronization pacing when operating in the normal and/or vasoactive modes. When in the vasodilation or vasoconstriction mode, the stimulation pulses may be delivered during a refractory period after a ventricular sense or pace for every cardiac cycle or for some specified fraction of cardiac cycles (e.g., every third cardiac cycle). In order to duty cycle the vasoconstriction and/or vasodilation modes, the device may be configured to use one or more entry and/or exit conditions in controlling entry and/or exit into the modes. An entry or exit condition could be, for example, lapsed time intervals (e.g., specified time(s) of the day or the lapsed time since a particular event), actuation of a switch by the patient (e.g., a magnetically or tactilely actuated switch interfaced to the device controller), a command received via telemetry, or a measured variable being within or out of a specified range. Examples of such measured variables include feature(s) derived from an electrogram indicative of myocardial ischemia, heart rate, activity level, minute ventilation, cardiac output, blood pressure, blood oxygen, blood pH, and myocardial contractility (e.g., as indicated by the maximum dP/dt measured by an arterial pressure sensor). A plurality of entry and/or exit conditions may also be logically ORed or ANDed together to form a composite exit or entry condition. FIG. 6 shows an exemplary algorithm that the device controller executes to switch from a normal mode to one of the vasoconstriction and vasodilation modes. At step 601, the device determines if an entry condition for switching to a particular vasoactive mode are met. If so, the device checks to see if an exit condition for that vasoactive mode are met at step 602. If so, the device returns to step 601. Otherwise the device executes the mode switch to the vasoactive mode at step 603 and proceeds to step 604 to monitor for an exit condition. If an exit condition is met, the device reverts to the normal mode at step 605 and returns to step 601 to monitor for an entry condition.

Figure 7:
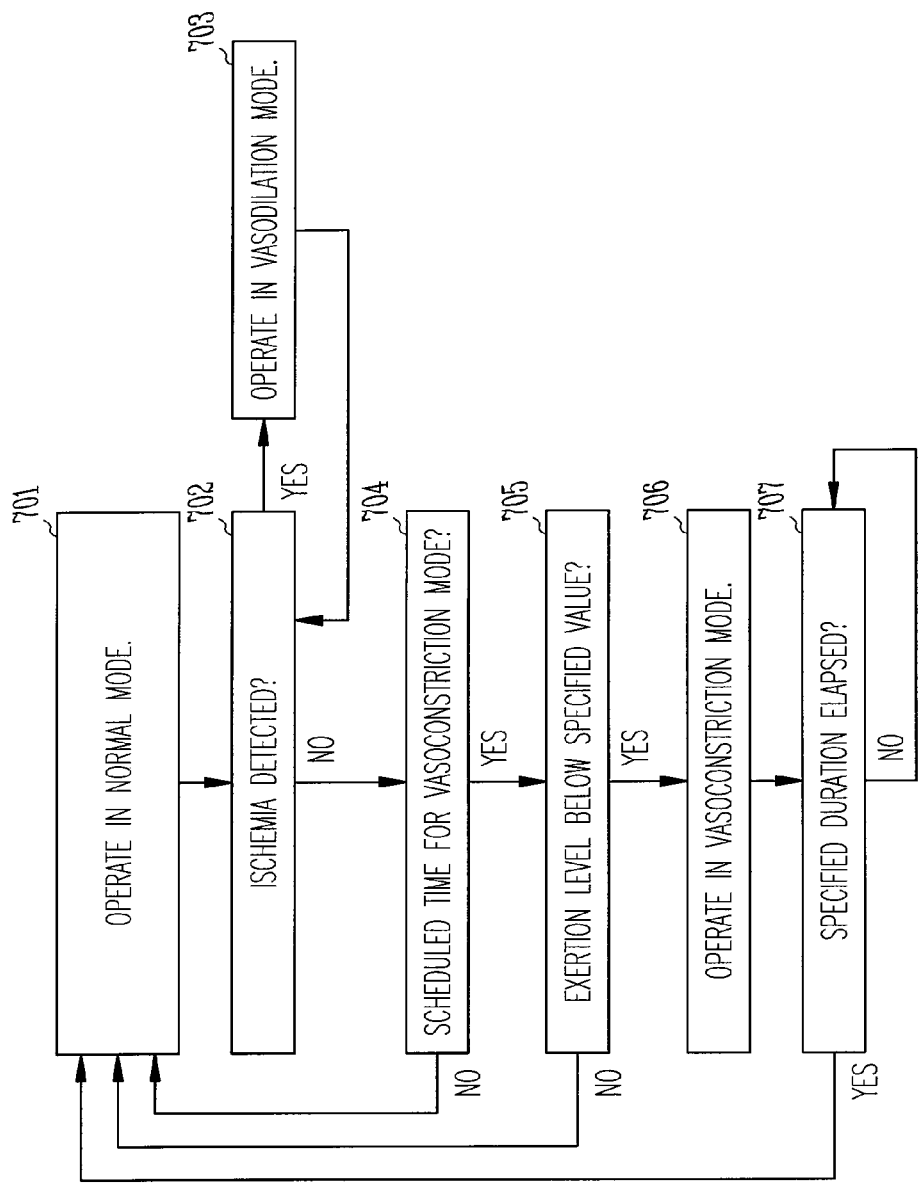
FIG. 7 illustrates an exemplary algorithm for switching between a normal mode, a vasoconstriction mode, and a vasodilation mode.

In an example embodiment, the device is equipped with one or more sensors for sensing a variable that can be correlated with the occurrence of myocardial ischemia and programmed to detect the presence or absence of myocardial ischemia in accordance with the sensed variable. The sensor(s) may be a cardiac sensing channel for recording electrograms and measuring heart rate, an accelerometer for measuring activity level or local cardiac motion, an impedance sensor sensitive to local changes in tissue impedance that occur during ischemia, and/or a minute ventilation sensor. The device is then configured to operate in a normal mode when no vasoactive therapy is being delivered and to switch to the vasodilation mode and/or vasoconstriction mode in response to sensed conditions and/or a patient-initiated command. For example, the device may intermittently switch to the vasoconstriction mode according to a defined schedule but only if the sensed variable indicates the absence of myocardial ischemia. For example, the device may sense the patient's exertion level (e.g., as reflected by heart rate, activity level, and/or minute ventilation) and be configured to intermittently switch to the vasoconstriction mode only if the sensed variable is within a specified range. The controller is then programmed to switch to the vasodilation mode whenever the sensed variable indicates the presence of myocardial ischemia and operate intermittently in either the vasoconstriction mode or the normal mode whenever the sensed variable indicates the absence of myocardial ischemia. The device could also be configured to switch from the normal mode to the vasodilation mode if the sensed variable indicates the presence of myocardial ischemia. FIG. 7 illustrates an example algorithm that could be executed by the controller to switch between the normal mode and the vasoconstriction and vasodilation modes. At step 701, the device operates in the normal mode, which may entail delivering some kind of pacing therapy (e.g., bradycardia or resynchronization pacing) or delivering no pacing at all. At step 702, the device checks for the presence of ischemia. If myocardial ischemia is detected, the device operates in the vasodilation mode at step 703 for as long as the ischemia is present. If myocardial ischemia is not present, the device checks to see if it is time to switch to the vasoconstriction mode at step 704. If so, the device determines at step 705 if the measured exertion level is below a specified value that indicates the patient is at rest. If the patient is at rest, the device operates in the vasoconstriction mode at step 706 and remains in that mode until a specified duration has elapsed as determined at step 707. In another embodiment, the patient is provided with a means for switching the device to the vasoconstriction mode, to the vasodilation mode upon experiencing symptoms of myocardial ischemia, and/or to a normal mode. Such a means, for example, may be a patient-operated switch interfaced to the device controller such as a magnetically-actuated or tactilely-actuated switch. The patient may also be provided with a means for communicating to the device via telemetry, such as from a remote monitor, in order to issue a command to switch to a selected mode.

In another embodiment, a myocardial region vulnerable to becoming ischemic is identified anatomically. An area of ischemia can be identified by a number of means, including ultrasonic imaging, PET scans, thallium scans, and MRI perfusion scans. A stimulation lead (e.g., a screw-in lead) is then strategically placed so as to stimulate the myocardial capillary bed that feeds the identified vulnerable region. The device may then be programmed to deliver vasodilation stimulation to the capillary bed when myocardial ischemia is detected. Vasoactive therapy as described herein may also be combined with pacing therapy that alters regional wall stress for therapeutic effect. For example, regions of the myocardium in proximity to a paced site are pre-excited during systole so as to experience reduced wall stress and metabolic demand, while regions of the myocardium remote from the paced site experience increased wall stress and metabolic demand. Such pre-excitation pacing may be employed to intentionally stress a particular myocardial region for conditioning purposes and may be combined with vasoconstriction stimulation. Pre-excitation pacing may also be employed to mechanically unload a vulnerable myocardial region such as when myocardial ischemia is detected and may be combined with vasodilation stimulation.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A cardiac device, comprising:
   a pulse generator for outputting vasoactive stimulation pulses, wherein the pulse generator is connectable to a vasoactive stimulation electrode disposed in proximity to a coronary artery;
   a sensing amplifier for sensing cardiac electrical activity;
   an impedance sensor for measuring cardiac blood flow;
   a controller programmed to intermittently switch between a normal mode in which no vasoactive stimulation pulses are delivered or a vasodilation mode in which vasoactive stimulation pulses are delivered in a manner that causes vasodilation of the coronary artery; and,
   wherein the controller is further programmed to deliver vasoactive stimulation pulses in the vasodilation mode such that the delivery of vasoactive stimulation pulses is timed to occur coincidentally with mechanical ventricular diastole as determined from the measured cardiac blood flow.

2. The device of claim 1 wherein the controller is programmed to measure heart rate from the sensed cardiac electrical activity and to switch from the normal mode to the vasodilation mode if the heart rate reaches a value indicating myocardial ischemia in a particular patient.

3. The device of claim 1 further comprising:
   a patient-operated switch; and,
   wherein the controller is programmed to switch from the normal mode to the vasodilation mode upon actuation of the patient-operated switch.

4. The device of claim 1 further comprising:
   a telemetry transceiver; and,
   wherein the controller is programmed to switch from the normal mode to the vasodilation mode upon receipt of a telemetry command to do so.

5. The device of claim 1 further comprising:
   a sensor for sensing a variable that can be correlated with the occurrence of myocardial ischemia in a patient; and,
   wherein the controller is programmed to switch from the normal mode to the vasodilation mode when the sensed variable indicates myocardial ischemia.

6. The device of claim 5 wherein the sensed variable that can be correlated with the presence of myocardial ischemia is selected from a group that includes features derived from sensed cardiac electrical activity, minute ventilation, and activity level.

7. The device of claim 1 wherein the controller is programmed to switch from the vasodilation mode to the normal mode upon occurrence of a specified vasodilation exit condition and wherein the exit condition is selected from a group that includes non-detection of the presence of myocardial ischemia, a lapsed time interval, actuation of a patient-operated switch, and receipt of a telemetry command to terminate the mode.

8. The device of claim 1 wherein the controller is further programmed to operate in a vasoconstriction mode in which vasoactive stimulation pulses are delivered during a cardiac refractory period as determined from the sensed cardiac electrical activity in a manner that causes vasoconstriction of the coronary artery.

9. The device of claim 8 wherein the controller is programmed to intermittently switch from the normal mode or vasodilation mode to the vasoconstriction mode according to a defined schedule.

10. The device of claim 8 wherein the controller is programmed to exit the vasoconstriction mode if a measured heart rate or other variable reflective of exertion level is above a specified threshold value.

11. The device of claim 1 wherein the controller is programmed to deliver vasoactive stimulation pulses during a cardiac refractory period as determined from the sensed cardiac electrical activity.

12. A method, comprising:
    implanting a pulse generator and an impedance sensor for measuring cardiac blood flow in a patient;
    implanting a vasoactive stimulation electrode connected to the pulse generator near a coronary artery and delivering vasoactive stimulation pulses to the coronary artery;
    programming the pulse generator to intermittently switch between a normal mode in which no vasoactive stimulation pulses are delivered or a vasodilation mode in which vasoactive stimulation pulses are delivered in a manner that causes vasodilation of the coronary artery; and,
    further programming the pulse generator such that the delivery of vasoactive stimulation pulses in the vasodilation mode is timed to occur coincidentally with mechanical ventricular diastole as determined from the measured cardiac blood flow.

13. The method of claim 12 further comprising programming the pulse generator to measure heart rate from the sensed cardiac electrical activity and to switch from the normal mode to the vasodilation mode if the heart rate reaches a value indicating myocardial ischemia in a particular patient.

14. The method of claim 12 further comprising programming the pulse generator to switch from the normal mode to the vasodilation mode upon actuation of a patient-operated switch.

15. The method of claim 12 further comprising programming the pulse generator to switch from the normal mode to the vasodilation mode upon receipt of a telemetry command to do so.

16. The method of claim 12 further comprising programming the pulse generator to switch from the normal mode to the vasodilation mode when a sensed variable indicates myocardial ischemia.

17. The method of claim 16 wherein the sensed variable indicative of the presence of myocardial ischemia is selected from a group that includes features derived from sensed cardiac electrical activity, mechanical activity, minute ventilation, and activity level.

18. The method of claim 12 further comprising programming the pulse generator to switch from the vasodilation mode to the normal mode upon occurrence of a specified vasodilation exit condition and wherein the exit condition is selected from a group that includes non-detection of the presence of myocardial ischemia, a lapsed time interval, actuation of a patient-operated switch, and receipt of a telemetry command to terminate the mode.

19. The method of claim 12 further comprising programming the pulse generator to operate in a vasoconstriction mode in which vasoactive stimulation pulses are delivered during a cardiac refractory period as determined from the sensed cardiac electrical activity in a manner that causes vasoconstriction of the coronary artery.

20. The method of claim 19 further comprising programming the pulse generator to intermittently switch from the normal mode or vasodilation mode to the vasoconstriction mode according to a defined schedule.

21. The method of claim 19 further comprising programming the pulse generator to exit the vasoconstriction mode if a measured heart rate or other variable reflective of exertion level is above a specified threshold value.

22. The method of claim 12 further comprising delivering vasoactive stimulation pulses during a cardiac refractory period as determined from sensed cardiac electrical activity.

\* \* \* \* \*